United States Patent
Peterson

(10) Patent No.: US 9,439,611 B2
(45) Date of Patent: Sep. 13, 2016

(54) DIGITAL RETROFIT SYSTEM AND METHOD FOR X-RAY RADIOGRAPHY

(75) Inventor: Drew Clark Peterson, Garner, NC (US)

(73) Assignee: Viztek, LLC, Garner, NC (US)

(*) Notice: Subject to any disclaimer, the term of this patent is extended or adjusted under 35 U.S.C. 154(b) by 387 days.

(21) Appl. No.: 13/536,117

(22) Filed: Jun. 28, 2012

(65) Prior Publication Data

US 2013/0003933 A1     Jan. 3, 2013

Related U.S. Application Data

(60) Provisional application No. 61/502,576, filed on Jun. 29, 2011.

(51) Int. Cl.
    *A61B 6/00*            (2006.01)

(52) U.S. Cl.
CPC . *A61B 6/40* (2013.01); *A61B 6/42* (2013.01); *A61B 6/542* (2013.01); *A61B 6/548* (2013.01); *A61B 6/56* (2013.01)

(58) Field of Classification Search
CPC ...... A61B 6/467; A61B 6/545; A61B 6/548; A61B 6/4233; A61B 6/4429; A61B 6/40; A61B 6/42; A61B 6/542; A61B 6/56; G01N 23/04; G01T 1/20
USPC ........... 378/91, 98, 98.8, 114, 115, 116, 117, 378/207
See application file for complete search history.

(56) References Cited

U.S. PATENT DOCUMENTS

| | | | |
|---|---|---|---|
| 6,201,318 B1 | 3/2001 | Guillory | |
| 6,584,171 B2 | 6/2003 | Suzuki et al. | |
| 7,154,994 B2 | 12/2006 | Gray | |
| 7,573,979 B2 | 8/2009 | Taoka et al. | |
| 7,844,031 B2 | 11/2010 | Newman et al. | |
| 8,085,901 B2 | 12/2011 | Newman et al. | |
| 2006/0242094 A1 | 10/2006 | Tamakoshi | |
| 2008/0198969 A1* | 8/2008 | Taoka et al. | 378/98 |
| 2009/0129546 A1* | 5/2009 | Newman et al. | 378/114 |
| 2011/0123001 A1* | 5/2011 | Kopcienski | A61B 6/4405 378/198 |

FOREIGN PATENT DOCUMENTS

| | | |
|---|---|---|
| CN | 101868181 A | 10/2010 |
| WO | 2009/067189 A1 | 5/2009 |

OTHER PUBLICATIONS

International Search Report and Written Opinion dated Sep. 17, 2012 from corresponding PCT/US2012/044600.

(Continued)

*Primary Examiner* — Glen Kao

(74) *Attorney, Agent, or Firm* — Ohlandt, Greeley, Ruggiero & Perle, L.L.P.

(57) ABSTRACT

There is provided a method that includes (a) detecting, at a point on a cable that runs from a controller to an x-ray generator, a prepare signal that is being transmitted from the controller to the x-ray generator to prepare the x-ray generator to generate an x-ray, and (b) transmitting, in response to the detecting, an initialize signal that causes a reset of a digital receiver panel that prepares the digital receiver panel to capture the x-ray. There is also provided a system that performs the method, and a storage device that controls a processor to execute the method.

16 Claims, 17 Drawing Sheets

(56) References Cited

OTHER PUBLICATIONS

International Preliminary Report on Patentability dated Oct. 16, 2013 corresponding to PCT/US12/44600, 21 pp.

Chinese Office Action dated Aug. 25, 2015 from corresponding Chinese Application No. 2012800322786 with English translation, 11 pages.

* cited by examiner

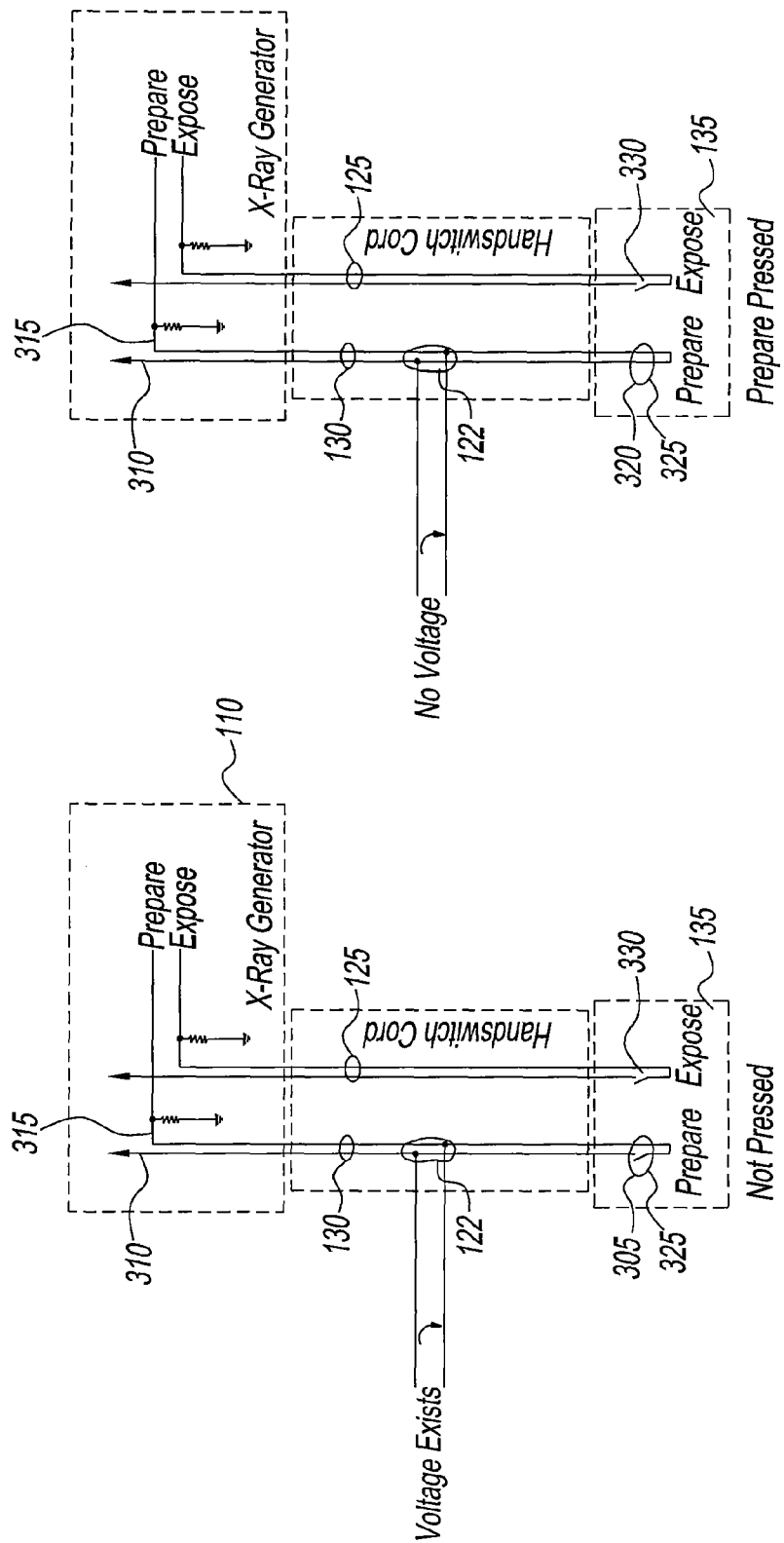

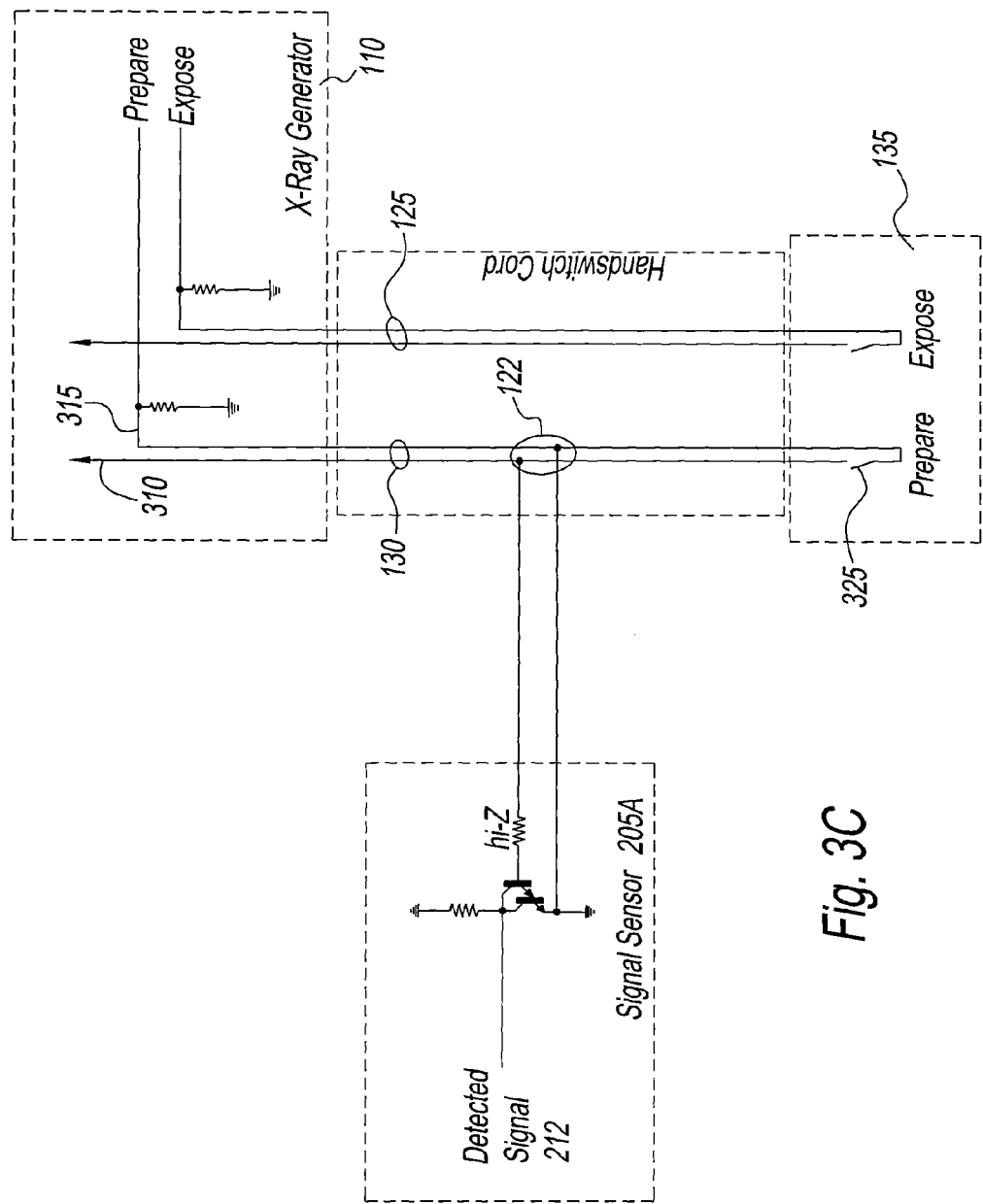

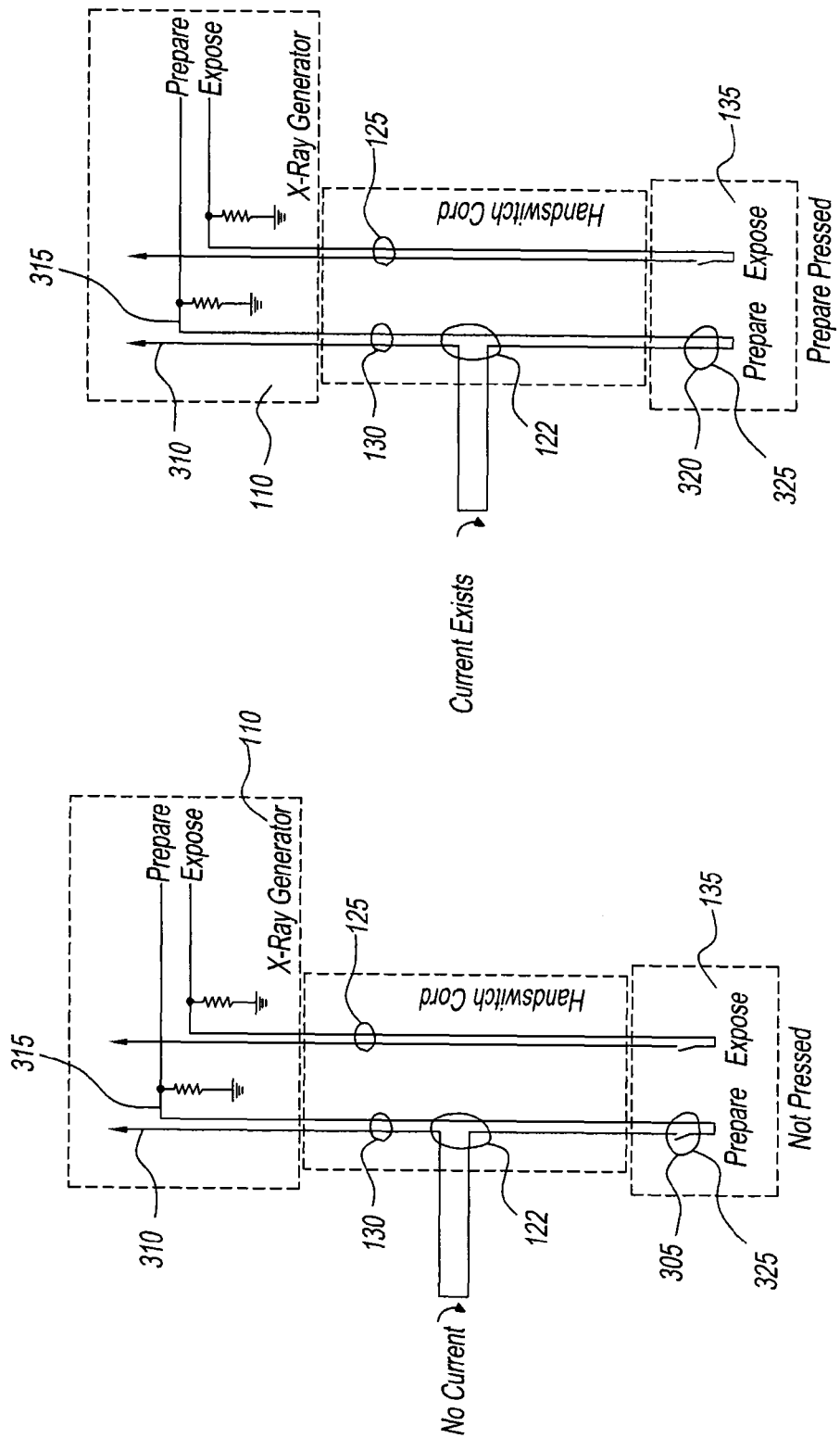

DIGITAL RETROFIT SYSTEM AND METHOD FOR X-RAY RADIOGRAPHY

BACKGROUND

1. Field of the Disclosure

The present disclosure relates to x-ray machines, and more particularly, to retrofitting an existing x-ray system having an x-ray generator with a retrofit device, where the retrofit device resets a digital receiver panel in preparation for illumination by an x-ray exposure from the x-ray generator. The retrofit device provides for detecting an x-ray preparation signal so that the digital x-ray detector may be initialized to receive the x-ray exposure. The retrofit device is compatible with a variety of x-ray preparation signal characteristics and does not alter a preexisting x-ray preparation signal, thereby removing the need to modify existing equipment, and preserving the existing equipment's original functional characteristics. The retrofit device also includes provisions for conditioning the received x-ray preparation signal, before transmitting a further control signal to the digital x-ray detector, to enhance compatibility with various x-ray generators.

2. Description of the Related Art

Digital radiography systems capture radiation of an x-ray exposure on photo-sensitive layers of a digital x-ray receiver panel. The photo-sensitive layers, when read by a computer, provide an image of an internal structure of an exposed area, i.e., a digital x-ray image, on a digital screen, e.g., a computer screen. The digital x-ray image is stored in a database for subsequent access. In addition, the digitally rendered x-ray picture can be transmitted to remote locations for analysis and diagnosis from a radiologist.

Digital radiography provides desirable benefits over conventional systems that utilize film or cassette technologies. However, with digital radiography, a digital x-ray receiver panel must be reset prior to an x-ray exposure. This reset alleviates unwanted noise from the photo-sensitive layers of the digital x-ray receiver panel and mitigates against additional exposures due to noisy, or inaccurate, x-ray images.

Many types of digital x-ray detectors require synchronization with each x-ray exposure. These detectors must receive a signal in advance, so they can become ready to capture an x-ray. Some of these detectors also depend on the signal to remain active throughout the entire duration of the x-ray exposure, while other detectors will automatically stop capturing after a predetermined time (e.g., length of maximum-duration exposure). To ensure both patient safety and proper image quality, the detector must receive the signal a minimum amount of time before the possibility of x-ray exposure, to ensure that no x-ray radiation is produced while the detector is not ready to receive it.

Most full-size x-ray generators support signal integration intended for reciprocating buckys, typically referred to as a Bucky Interface, which already conforms to the synchronization requirements of such digital x-ray detectors. However in the realm of mobile x-ray imaging, where x-ray generators are downsized and reciprocating buckys are considered too bulky for their possible benefits, x-ray generator manufacturers have left out support for such signal integration.

The fact that the digital x-ray detector consumes electrical power through its initialization input means that it could prevent the x-ray generator from recognizing the preparation signal, if routed directly through the detector's input. As well, the fact that the digital x-ray detector's initialization input may require specific electrical characteristics (e.g. voltage, timing) that are different from the x-ray generator's preparation signal means the signal may not be compatible, if routed directly.

Therefore, to retrofit a digital x-ray detector requiring synchronization to an x-ray generator that does not support sending signals to such an external device, a creative approach is necessary. An ideal solution is one that does not require operational or constructional modifications to the x-ray generator or digital x-ray detector, yet where all x-ray radiation produced during an exposure event contributes to developing a digital x-ray image.

U.S. Pat. No. 7,844,031 to Newman et al. is directed to an apparatus that adapts a preexisting system that includes a conventional film-based and/or computed radiography x-ray imaging system, for use with a retrofit digital radiography detector. The apparatus includes an interface and control circuit that interfaces with the digital radiography detector and an x-ray generator. However, the interface and control circuit must either be installed between a preexisting operator controller and the x-ray generator, or replace the preexisting operator controller. Thus, the use of the apparatus requires a modification of the preexisting system and possibly alters electrical characteristics of signals that would ordinarily be transmitted from the preexisting operator controller to the x-ray generator.

SUMMARY

There is a need for a retrofit device that detects the presence of an x-ray preparation signal without altering its electrical characteristics, and retransmits it to a digital x-ray detector, at appropriate electrical characteristics as required by the detector. Accordingly, there is provided a retrofit device that performs operations of (a) detecting, at a point on a cable that runs from a controller to an x-ray generator, a prepare signal that is being transmitted from the controller to the x-ray generator to prepare the x-ray generator to generate an x-ray, and (b) transmitting, in response to the detecting, an initialize signal that causes a reset of a digital receiver panel that prepares the digital receiver panel to capture the x-ray.

Additionally, in a situation that the x-ray generator does not require the presence of the x-ray preparation signal throughout its entire exposure event, yet the digital x-ray detector does require the signal throughout the entire exposure event, the retrofit device will extend its retransmission of the preparation signal by a predetermined amount of time, e.g., length of maximum-duration exposure.

BRIEF DESCRIPTION OF THE DRAWINGS

FIGS. 3A-3C are schematic diagrams that illustrate a technique for detecting a prepare signal by way of a voltage measurement.

FIGS. 4A-4C are schematic diagrams that illustrate a technique for detecting a prepare signal by way of a current measurement.

A component or a feature that is common to more than one drawing is indicated with the same reference number in each of the drawings.

DETAILED DESCRIPTION

The present document discloses an apparatus, i.e., a retrofit device, for digital x-ray radiography. The retrofit device detects an x-ray preparation signal, and as a result of such detection, initializes, e.g., resets, a digital x-ray receiver prior to an x-ray exposure. The retrofit device employs methods of non-invasive detection that maintain the integrity of a detected signal, and thus preserves the integrity and functional characteristics of original equipment.

There is a characteristic that exists with all currently-known x-ray generator systems: a certain amount of preparation time must expire before an x-ray exposure can occur. The reason and mechanisms of this delay may vary, but typically involve generation of high voltages and/or mechanical actuation of x-ray tube components. Since the delay must inevitably occur before x-ray radiation can be produced, it is similar to the characteristic of such digital x-ray detectors that also must be prepared before receiving x-ray radiation.

The pre-exposure delay exhibited by the x-ray generator is always longer than the pre-exposure delay required by the digital x-ray detector. This guarantees that if the signal that begins the x-ray generator preparation is also used to initialize the digital x-ray detector, there is no possibility of producing x-ray radiation before the digital x-ray detector is ready to receive it. By exploiting the x-ray preparation signal in this way, the x-ray exposure synchronization requirements may be met without operationally or constructionally modifying the x-ray generator or digital x-ray detector.

A benefit of the retrofit device is that it can be utilized to artificially delay the retransmission of the signal to the detector. Since the x-ray generator's preparation delay is longer than the detector's preparation delay, the new device can delay the retransmission by the difference in these times, thereby preventing the detector from becoming ready long before the x-ray generator is. This prevents the unnecessary introduction of signal noise which would otherwise be contributed into each digital x-ray image.

It is possible to detect the x-ray preparation signal at any point along its electrical path; however the cord that connects the operator's handswitch to the x-ray generator is the most accessible. It is also possible to detect the x-ray preparation signal without altering it, by performing measurements, of varying kinds, and detecting a change in measured values.

Figure 1:
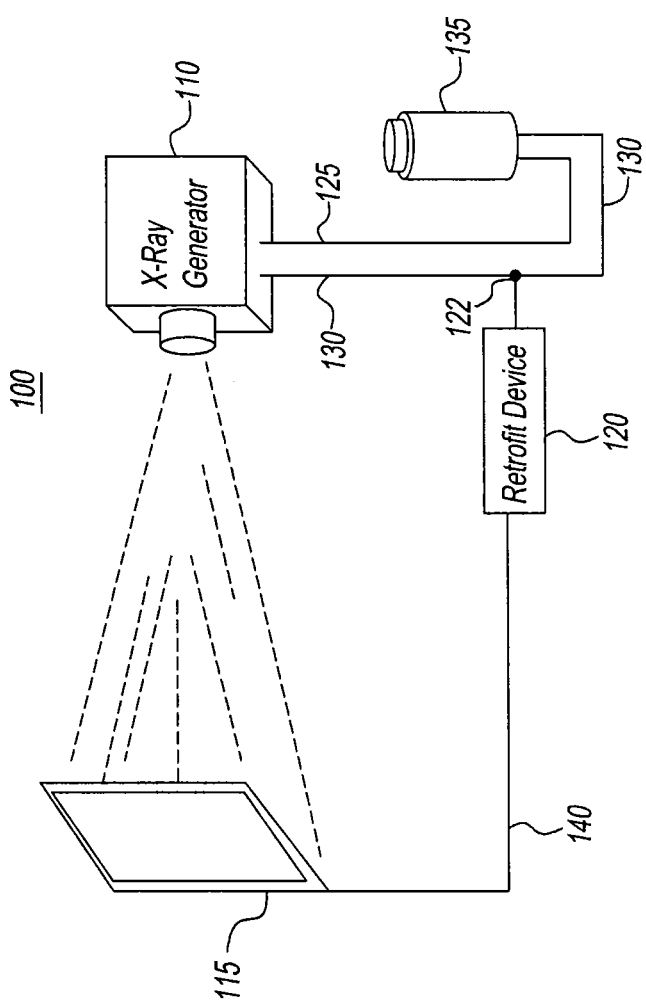
FIG. 1 is a block diagram of a digital retrofit x-ray system.

FIG. 1 is a block diagram of a digital retrofit x-ray system, e.g., system 100. System 100 includes an operator controller 135, an x-ray generator 110, a receiver panel 115, and a retrofit device 120. FIG. 1 also shows an expose signal 125, a prepare signal 130, an initialize signal 140, and a node 122.

Operator controller 135 is a switching device adapted to generate expose signal 125 and prepare signal 130. A cable, also referred to as a handset cord, runs between operator controller 135 and x-ray generator 110, and couples prepare signal 130 and expose signal 125 from operator controller 135 to x-ray generator 110.

X-ray generator 110, in response to a receipt of prepare signal 130, builds a charge to produce an x-ray, and in response to a receipt of expose signal 125, produces the x-ray.

Node 122 is a detection node, at a point on the cable that runs between operator controller 135 and x-ray generator 110, that retrofit device 120 monitors. Node 122 can be located at any point along the cable.

Retrofit device 120 is an apparatus that detects prepare signal 130 at node 122 and, as a result, generates initialize signal 140, and transmits initialize signal 140 to receiver panel 115.

Receiver panel 115 is a digital receiver panel that captures an x-ray and produces image data that represents the captured x-ray. In response to a receipt of initialize signal 140, receiver panel 115 performs a reset operation that prepares receiver panel 115 to capture the x-ray. For example, receiver panel 115, upon receipt of initialize signal 140, performs a reset of photo-sensitive layers to clear any prior states, e.g., noise.

There is a period of time, e.g., an energization period, between the occurrence of prepare signal 130 and the generation of the x-ray, during which x-ray generator 110 builds an electric charge for production of the x-ray. This energization period occurs after the operator manipulates operator controller 135 to produce prepare signal 130, while the operator pauses, prior to manipulating operator controller 135 to produce expose signal 125. Receiver panel 115 is reset during this energization period.

In operation, an operator (e.g., a doctor, a nurse, or an x-ray technician) prepares a patient for an x-ray exposure. That is, the operator positions the patient, or a portion of the patient desired to be imaged, between x-ray generator 110 and receiver panel 115. After proper positioning, the operator manipulates operator controller 135 to produce prepare signal 130. Prepare signal 130 is transmitted directly to x-ray generator 110. X-ray generator 110 receives prepare signal 130 and builds the electric charge required for production of the x-ray.

The operator thereafter manipulates operator controller 135 to produce expose signal 125. Expose signal 125 is transmitted directly to x-ray generator 110. X-ray generator 110 receives expose signal 125 and, as a result, transmits the x-ray. Receiver panel 115 captures the x-ray, and produces image data that can be transmitted to a processor (not shown in FIG. 1) for printing and/or display on a display device (not shown in FIG. 1).

Figure 2:
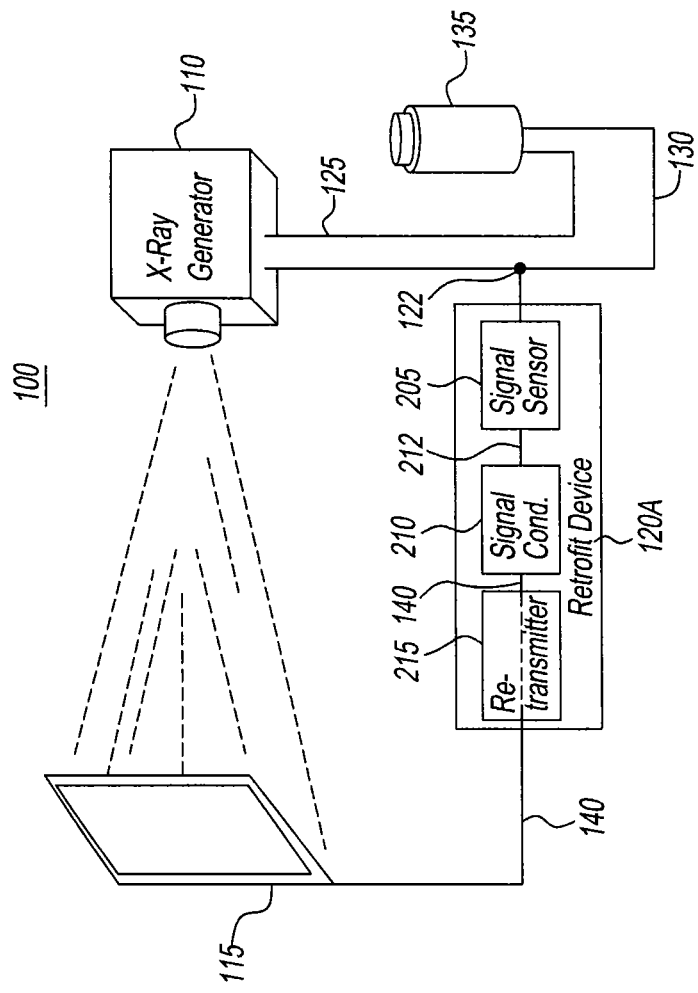
FIG. 2 is another block diagram of system the system of FIG. 1, showing an embodiment of retrofit device.

FIG. 2 is another block diagram of system 100, showing an embodiment of retrofit device 120, designated as a retrofit device 120A.

Retrofit device 120A includes a signal sensor 205 and a signal conditioner 210. Signal sensor 205 monitors node 122 to detect prepare signal 130. Signal sensor 205, upon detection of prepare signal 130, transmits a detected signal 212 to signal conditioner 210. Signal conditioner 210 receives and conditions detected signal 212, resulting in initialize signal 140, and transmits initialize signal 140 to a re-transmitter 215, which in turn transmits initialize signal 140 to receiver panel 115.

Preferably, signal sensor 205 maintains the integrity of prepare signal 130 by not introducing any electrical change to prepare signal 130. This, in turn, allows prepare signal 130 to be successfully transmitted from operator control 135 to x-ray generator 110 without any additional circuitry. Several techniques of detection are discussed below with reference to FIGS. 3A-3C and 4A-4C.

Components of retrofit device 120A are not confined to a particular physical embodiment. For example, wireless technology could be utilized, and as such, signal sensor 205 could be located remotely from a point of generation of initialize signal 140.

FIGS. 3A-3C are schematic diagrams that illustrate a technique for detecting prepare signal 130 by way of a voltage measurement. In particular, FIGS. 3A-3C illustrate a technique for detecting a change in voltage on prepare signal wiring. Operator controller 135, as illustrated, is a push button device having a prepare switch 325 that produces prepare signal 130, and an expose switch 330 that produces expose signal 125, but operator controller 135 could be any form of switching device that provides the functionality described herein.

FIG. 3A illustrates prepare switch 325 in an open position 305. In open position 305, a voltage exists between a prepare-active wire 310 and a prepare-ground wire 315. In open position 305 the voltage measured between prepare-active wire 310 and prepare-ground wire 315 is a constant value.

FIG. 3B illustrates prepare switch 325 in a closed position 320, which produces prepare signal 130. When prepare switch 325 is pushed into closed position 320, thereby closing the circuit between prepare-active wire 310 and prepare-ground wire 315, a voltage drop occurs between prepare-active wire 310 and prepare-ground wire 315. This voltage drop is recognized by signal sensor 205 and x-ray generator 110 as prepare signal 130.

FIG. 3C illustrates an embodiment of signal sensor 205, designated as a signal sensor 205A that detects prepare signal 130. Signal sensor 205A includes a high-impedance voltage circuit, in parallel with prepare-active wire 310 and prepare-ground wire 315, that detects prepare signal 130. The high-impedance voltage circuit includes a dual-transistor configuration ("Darlington Pair") that offers a substantial increase in sensitivity over a single transistor alone. This sensitivity allows the resistor (hi-Z) to be a high value and, thus, raises input impedance. Other technologies, such as, but not limited to, a Sziklai Pair or a Field-Effect Transistor (FET) could also be used in place of the Darlington Pair.

Signal sensor 205A operates in accordance with FIGS. 3A-3B and detects a change in voltage, e.g., a voltage drop signal, between prepare-active wire 310 and prepare-ground wire 315. When prepare switch 325 is in open position 305, there is a positive voltage on prepare-active wire 310, and a very small amount of current flows through the high impedance input of signal sensor 205A, through the base-emitter of its amplifying transistor, and returns, via node 122 to prepare-ground wire 315. This allows the transistor to conduct, and, thus, grounds detected signal 212. When prepare switch 325 is in closed position 320, prepare-active wire 310 and prepare-ground wire 315 are brought to the same electric potential, the transistor in signal sensor 205A turns OFF, and detected signal 212 is raised to a positive voltage, via a pull-up resistor. Accordingly, signal sensor 205A, after detecting prepare signal 130, produces detected signal 212, via inverting and amplifying the voltage drop of prepare signal 130.

Figure 4C:
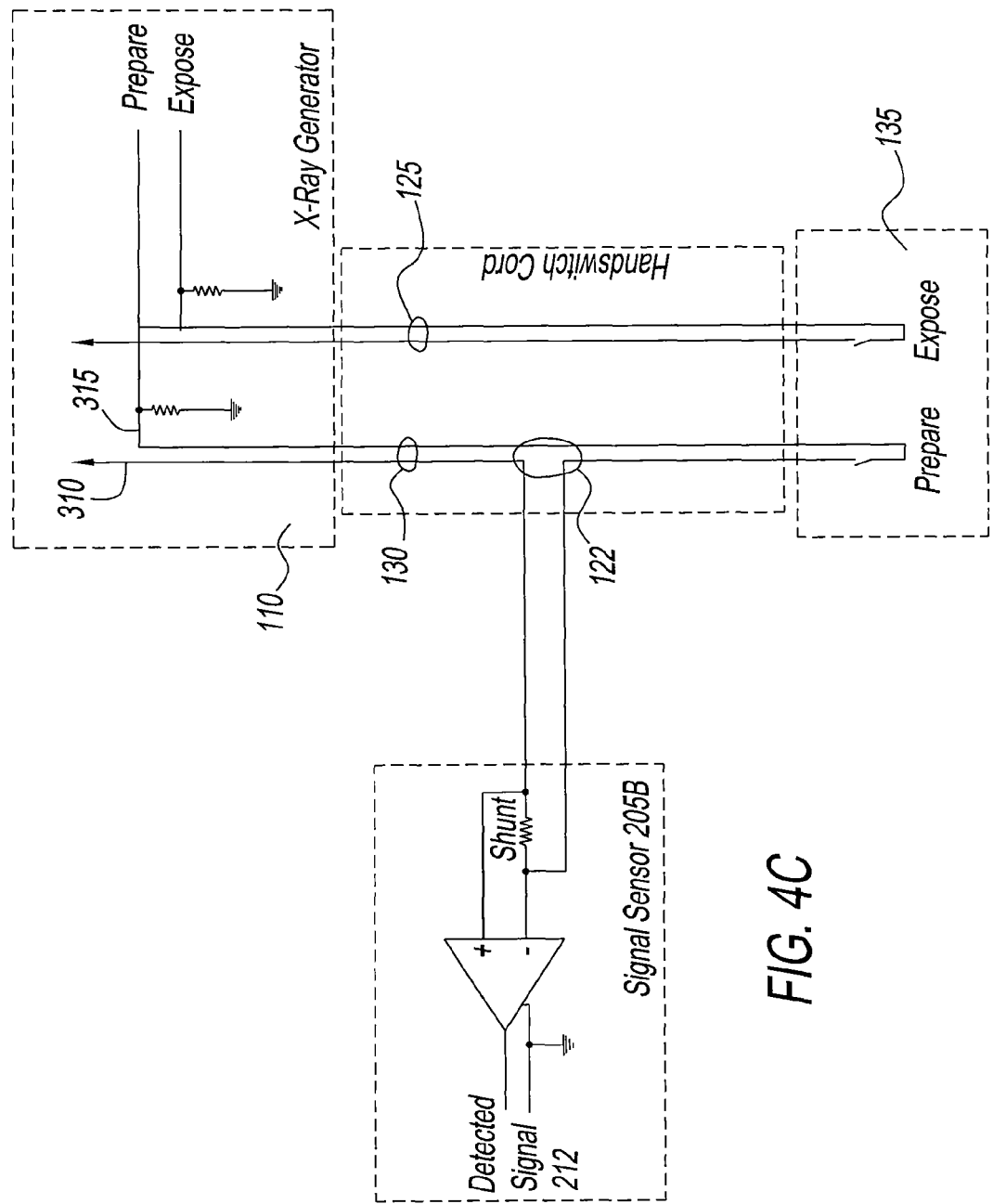

FIGS. 4A-4C are schematic diagrams that illustrate a technique for detecting prepare signal 130 by way of a current measurement. In particular, FIGS. 4A-4C illustrate how the system detects a change in current of a prepare signal wiring.

FIG. 4A, similar to FIG. 3A, illustrates prepare switch 325 in open position 305. In open position 305, there is no current produced on prepare-active wire 310, and thus, there is no current measured.

FIG. 4B, similar to FIG. 3B, illustrates prepare switch 325 in closed position 320, which produces prepare signal 130. When prepare switch 325 is in closed position 320, a current flows through prepare-active wire 310. This current flow is detected by signal sensor 205 and x-ray generator 110 as prepare signal 130.

FIG. 4C illustrates another embodiment of signal sensor 205, designated as a signal sensor 205B. In particular, FIG. 4C illustrates a circuit having a low-value resistor ("shunt") in combination with a current sensing circuit that detects prepare signal 130. This circuit operates in accordance with FIGS. 4A-4B and detects a change in current, e.g., current flow, on prepare-active wire 310. Further, signal sensor 205B, after detecting prepare signal 130, produces detected signal 212.

Figure 5:
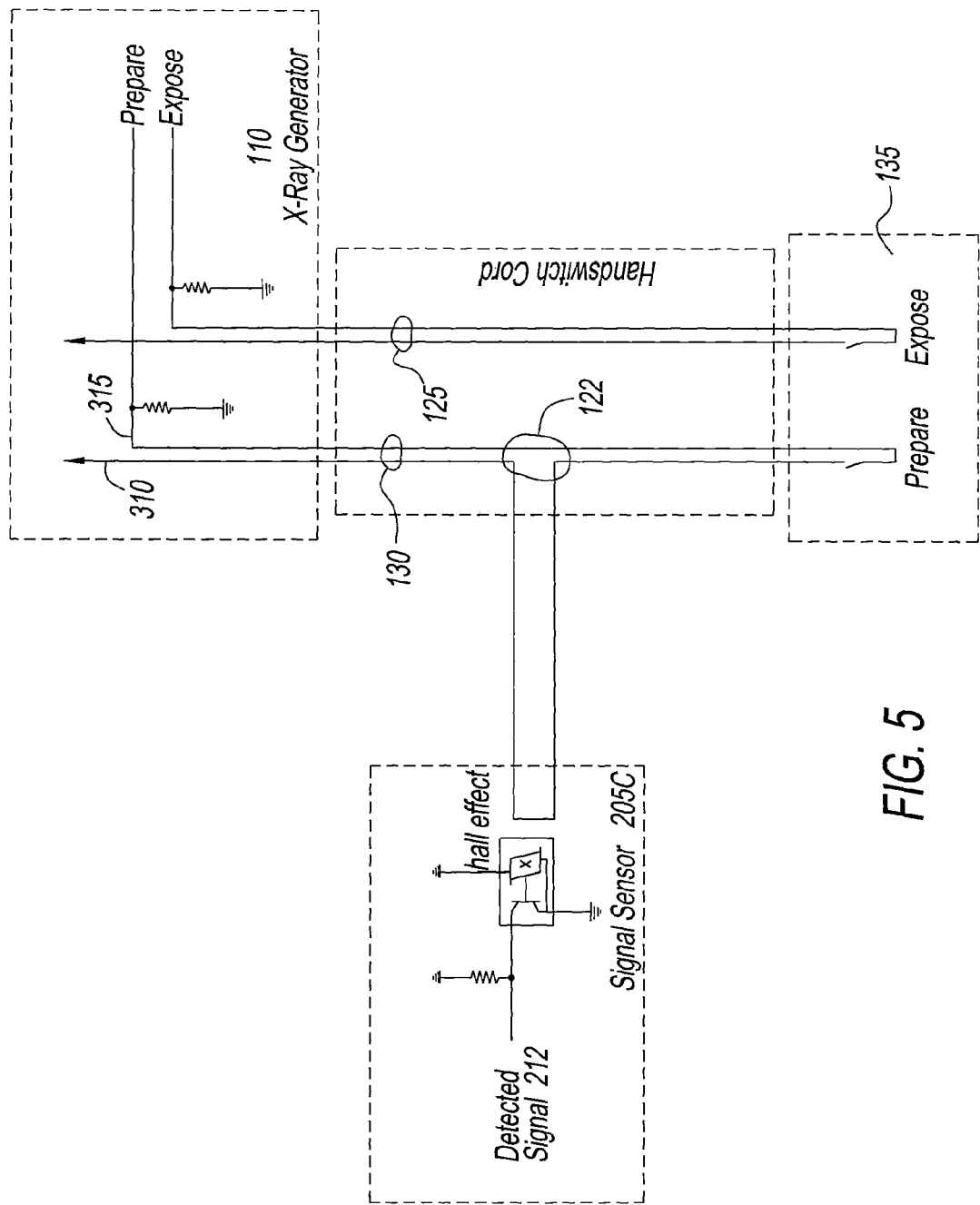
FIG. 5 is a schematic diagram that illustrates a technique for detecting a prepare signal by way of a magnetic field measurement.

FIG. 5 is a schematic diagram that illustrates a technique that employs an embodiment of signal sensor 205, designated as a signal sensor 205C, that detects prepare signal 130 by way of a magnetic field measurement. Signal sensor 205C detects the magnetic field surrounding prepare signal 130 wiring. Specifically, signal sensor 205C incorporates a hall-effect sensor that measures the magnetic field strength of prepare signal 130 wiring. Upon detection of a change in magnetic field, due to production of prepare signal 130, sensor 205C generates detected signal 212.

Figure 6:
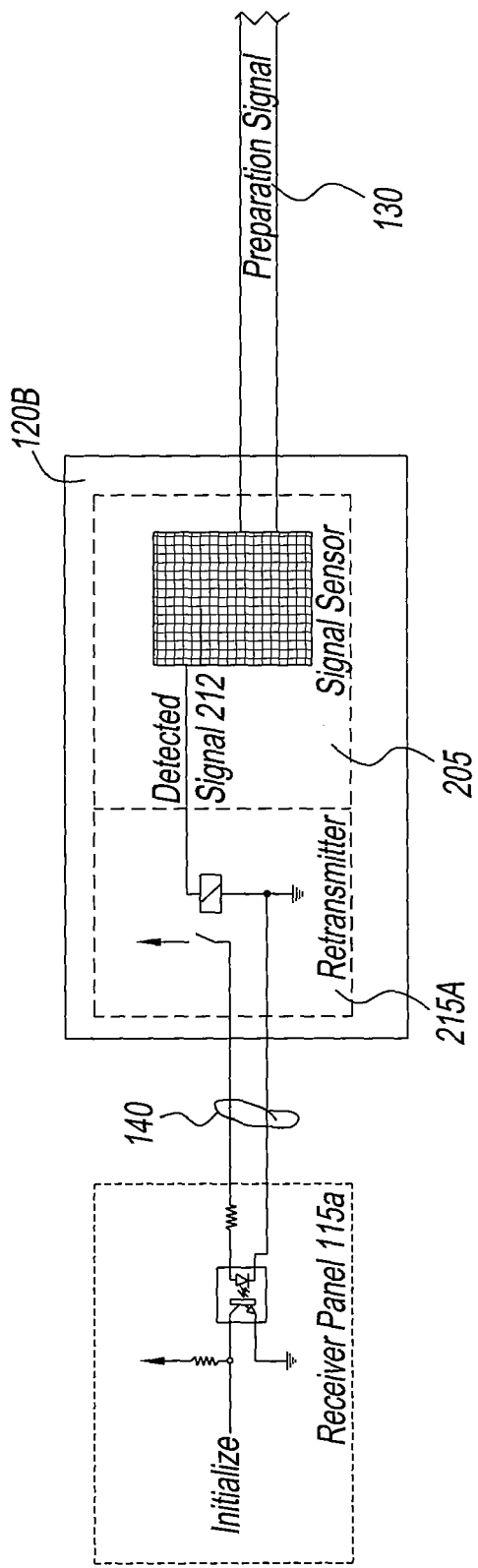
FIG. 6 is a schematic diagram that illustrates an embodiment of a receiver panel and a retrofit device of the system of FIG. 1.

FIG. 6 is a schematic diagram that illustrates embodiments of receiver panel 115 and retrofit device 120, designated as a receiver panel 115A and a retrofit device 120B, respectively. Retrofit device 120B includes signal sensor 205 and an embodiment of re-transmitter 215 designated as a re-transmitter 215A.

Retrofit device 120B senses prepare signal 130 via signal sensor 205, which, as a result of detection, transmits detected signal 212 to re-transmitter 215A. Re-transmitter 215A is a switching device (e.g., a transistor, relay, or repeater) that produces initialize signal 140, which is routed to receiver panel 115A. Re-transmitter 215A includes an amplifying circuit for detected signal 212 and is suited for situations where detected signal 212 is transmitted from a detection or conditioning circuit that operates at low voltage and/or from a circuit that can only source a small amount of current. Re-transmitter 215A amplifies detected signal 212, and further sources 24 volts with sufficient current to trigger receiver panel 115A.

In alternative embodiments, retrofit device 120 may sense prepare signal 130 via signal sensor 205 and, as a result of detection, transmit initialize signal 140 directly to receiver panel 115. That is, signal sensor 205 may be designed to generate and transmit initialize signal 140 as a result of detection, without any modification of the generated form of initialize signal 140. Alternatively, receiver panel 115 may be configured to receive detected signal 212. In this embodiment, detected signal 212 and initialize signal 140 are essentially the same signal, that is, detected signal 212 serves as initialize signal 140.

Figure 7A:
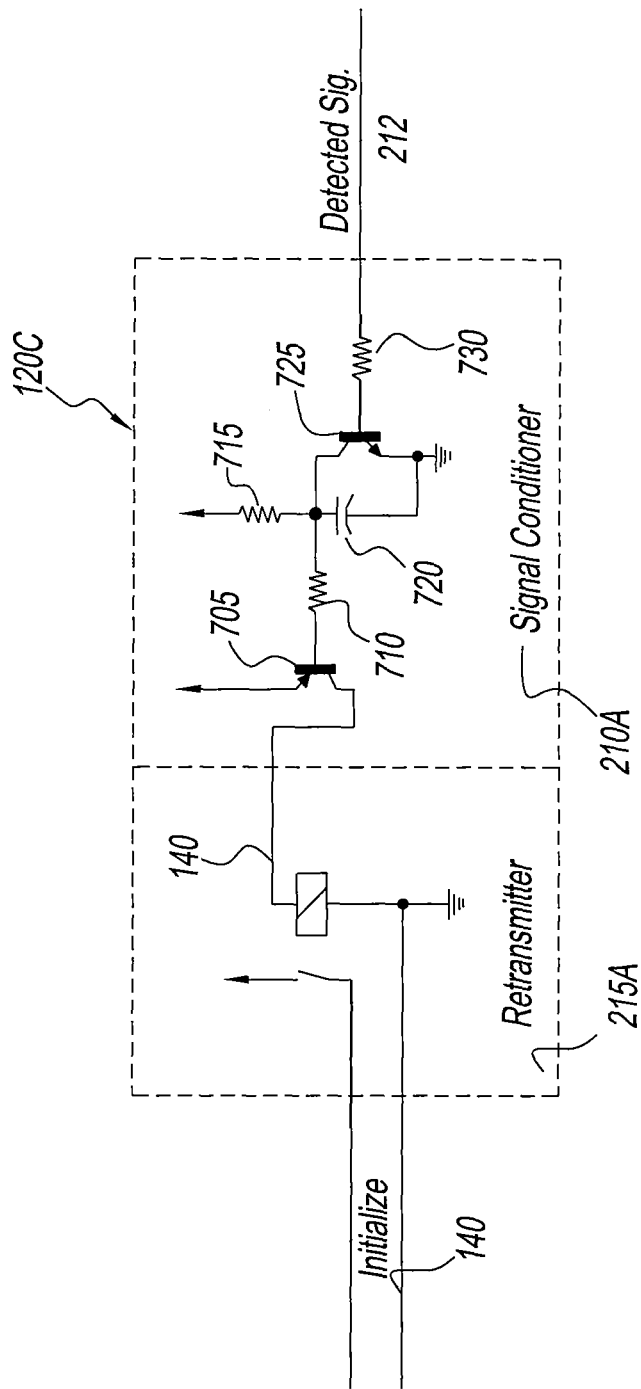
FIGS. 7A-7C are schematic diagrams of several embodiments of a retrofit device for a case where signal conditioning is necessary to produce an initialize signal that is compatible with a receiver panel.
Figure 7B:
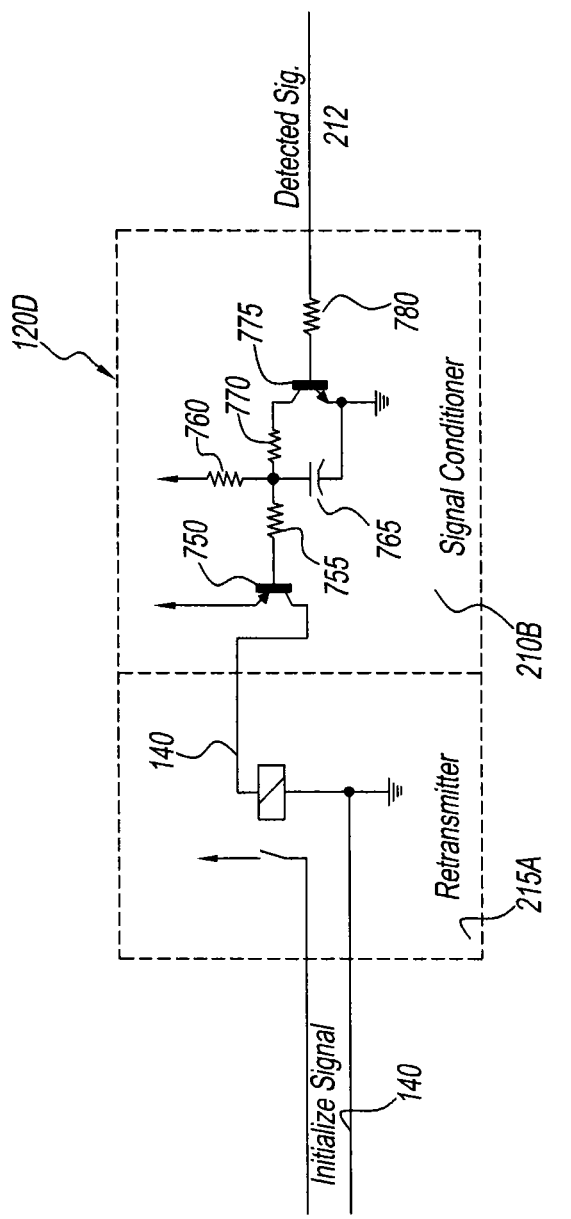
Figure 7C:
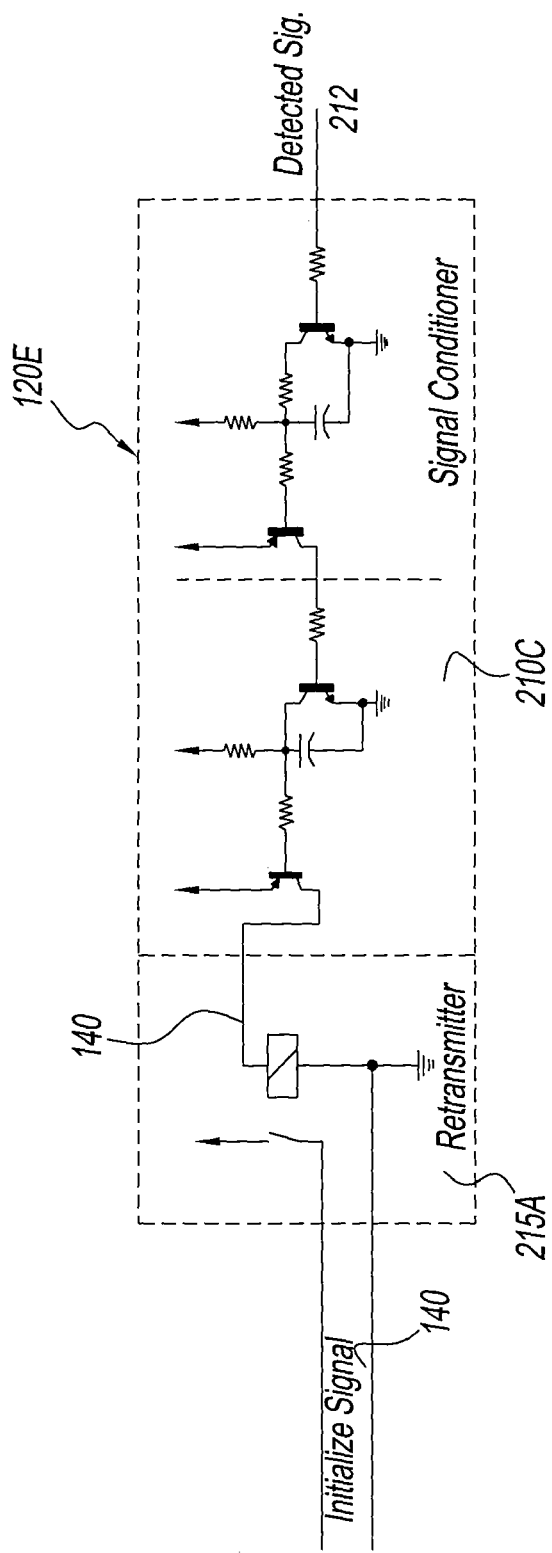

FIGS. 7A-7C are schematic diagrams of several embodiments of retrofit device 120, for a case where signal conditioning is necessary to produce initialize signal 140 that is compatible with receiver panel 115.

FIG. 7A is a schematic diagram of an embodiment of retrofit device 120, designated as a retrofit device 120C, that includes re-transmitter 215A, and an embodiment of signal conditioner 210 designated as a signal conditioner 210A. Signal conditioner 210A receives detected signal 212 from signal sensor 205 and transmits initialize signal 140 to re-transmitter 215A.

Figure 12:
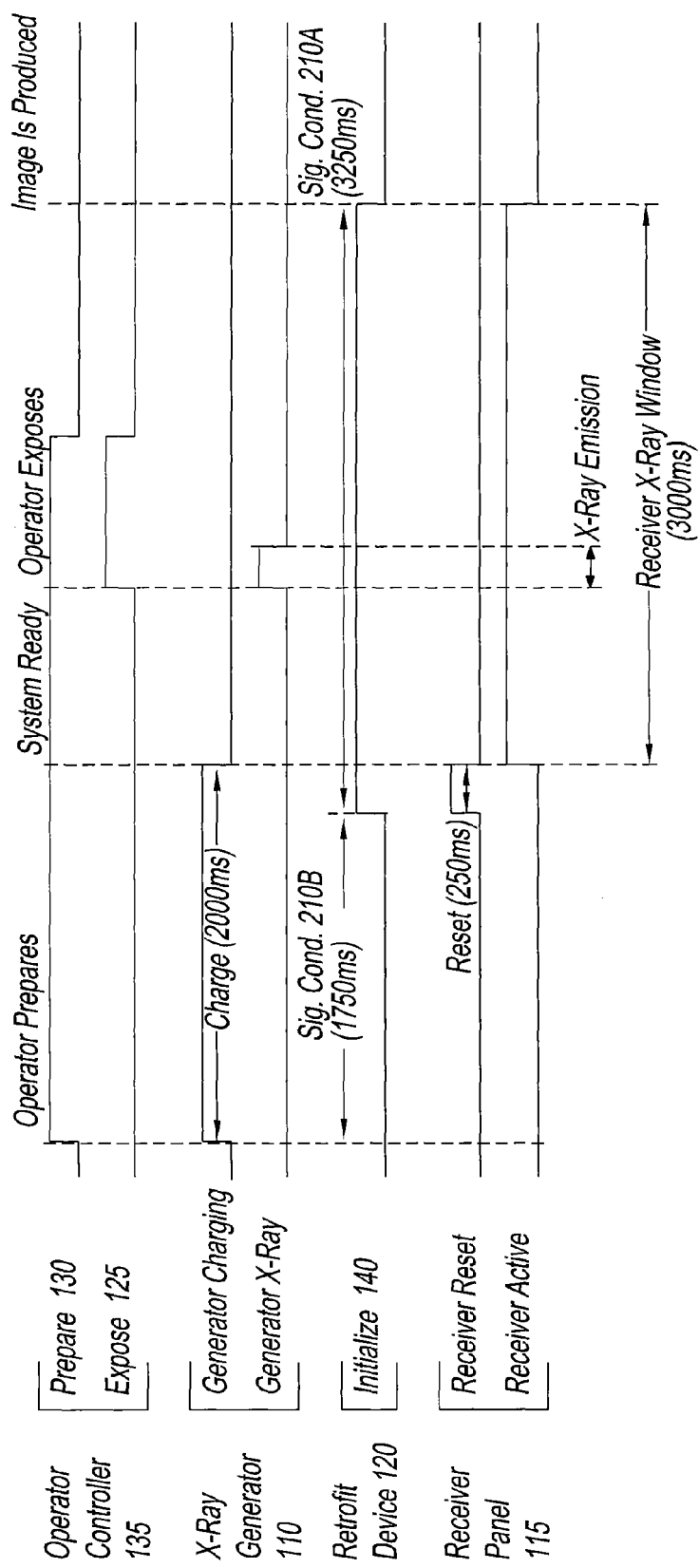
FIG. 12 is a timing diagram for several signals in the system of FIG. 1.

In some situations, receiver panel 115 may require that initialize signal 140 remain constant throughout the x-ray exposure while, in contrast, prepare signal 130 may be momentary, e.g., activated and deactivated prior to an x-ray exposure. Signal conditioner 210A maintains initialize signal 140 constant throughout an x-ray exposure. In this regard, signal conditioner 210A includes a timer circuit employed to maintain transmission of initialize signal 140 for a predetermined period of time, e.g., 3250 ms, that is equal to or greater than the period of time for the x-ray exposure. FIG. 12 is a timing diagram that shows these timing relationships.

When detected signal 212 is active, a positive voltage is applied via a resistor 730 to the base of a transistor 725, thus switching ON transistor 725. In turn, this shorts out a capacitor 720 that was previously charged through a pull-up resistor 715. Thus, a low voltage now exists, through a resistor 710, at the base of a transistor 705, which switches ON, and current flows via initialize signal 140 into the re-transmitter 215A. When detected signal 212 returns to an inactive state, transistor 725 turns OFF, and capacitor 720 begins to recharge through pull-up resistor 715. While capacitor 720 is not charged, a low voltage continues to exist at the base of transistor 705 that allows transistor 705 to keep sourcing current to re-transmitter 215A. Increasing the capacitance of capacitor 720 and/or increasing the resistance of pull-up resistor 715 will slow the rate of charging of capacitor 720 and thus keep initialize signal 140 active for a longer period of time after detected signal 212 becomes inactive. Preferably, the predetermined duration is equal to or greater than a maximum exposure duration of x-ray generator 110, to allow receiver panel 115 to properly receive the entire x-ray exposure.

FIG. 7B is a schematic of an embodiment of retrofit device 120, designated as a retrofit device 120D, that resets receiver panel 115 close-in-time to the exposure from x-ray generator 110. Retrofit device 120D includes re-transmitter 215A, and an embodiment of signal conditioner 210 designated as a signal conditioner 210B.

As discussed above, x-ray generator 110 receives prepare signal 130 and begins an energization period to build an electric charge required to produce an x-ray, i.e., an exposure. Transmitting initialize signal 140 close-in-time to the exposure, such that receiver panel 115 is reset just prior to the exposure, eliminates unwanted image data noise that can accrue at a receiver panel 115 prior to an x-ray exposure. Signal conditioner 210B provides a wait period to accomplish the close-in-time reset of receiver panel 115, via a timer circuit. Thus, after receipt of detected signal 212, signal conditioner 210B provides for a predetermined period of time to elapse before outputting initialize signal 140.

When detected signal 212 is active, a positive voltage is applied via a resistor 780 to the base of a transistor 775, which switches ON transistor 775. This allows a capacitor 765, which has previously been charged through a pull-up resistor 760, to slowly discharge through a resistor 770 and the collector of transistor 775. When capacitor 765 is sufficiently discharged, a low voltage exists at the base of a transistor 750, which turns ON transistor 750 and allows current to flow through the emitter-base junction of transistor 750 and through resistor 755, and also from the emitter to the collector of transistor 750, via initialize signal 140 into re-transmitter 215. Increasing the capacitance of capacitor 765 and/or increasing the resistance of resistor 770 will slow the rate of discharge of capacitor 765 and thus prevent initialize signal 140 from becoming active for a longer period of time after detected signal 212 becomes active. Preferably, signal conditioner 210B transmits initialize signal 140 at a time close to, but less than, the end of the energization period for x-ray generator 110. In addition, the time period for transmission of initialize signal 140 may depend on the reset time period for receiver panel 115. For example, x-ray generator 110 may have an energization period of 2000 milliseconds (ms), to build the necessary charge, and receiver panel 115 may have a 250 ms reset period. In this example, signal conditioner 210B waits for 1750 ms before transmitting initialize signal 140, to accommodate the 2000 ms energization period of x-ray generator 110, and the 250 ms reset period of receiver panel 115. FIG. 12 is a timing diagram that shows these timing relationships.

FIG. 7C is a schematic of an embodiment of retrofit device 120, designated as a retrofit device 120E, that includes re-transmitter 215A, and an embodiment of signal conditioner 210 designated as a signal conditioner 210C. Signal conditioner 210C combines the functionality of signal conditioner 210A and signal conditioner 210B. More specifically, signal conditioner 210C maintains initialize signal 140 constant throughout the exposure and also provides a wait period before initial transmission of initialize signal 140.

Figure 8:
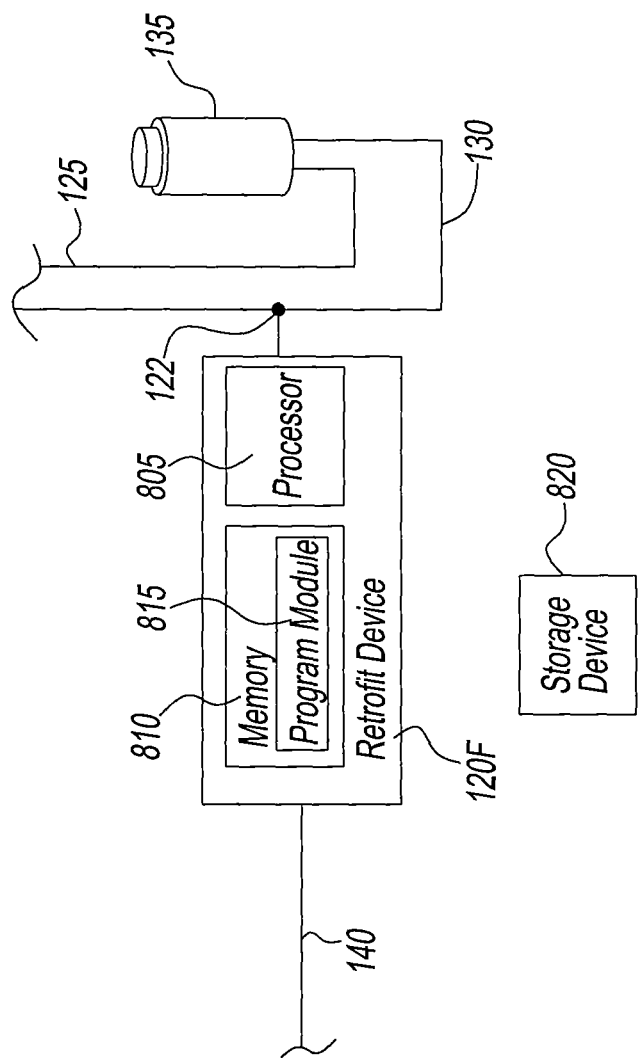
FIG. 8 is a block diagram of a retrofit device embodied in a computer device.

FIG. 8 is a block diagram that illustrates another embodiment of retrofit device 120, designated as a retrofit device 120F. Retrofit device 120F is a computer device capable of performing part, or all of the above discussed functionality of retrofit device 120 and its several embodiments, i.e., retrofit devices 120A-120E. Retrofit device 120F includes a processor 805 and a memory 810. Processor 805 is configured of logic circuitry (not shown) that responds to and executes instructions. Memory 810 is a tangible computer-readable storage device encoded with a program. In this regard, memory 810 stores data and instructions that are readable and executable by processor 805 for controlling the operation of processor 805. Memory 810 may be implemented in a random access memory (RAM), a hard drive, a read only memory (ROM), or a combination thereof. One of the components of memory 810 is a program module 815.

Program module 815 contains instructions for controlling processor 805 to execute the methods employed by the several embodiments of retrofit device 120 described herein. For example, under control of program module 815, processor 805 can detect prepare signal 130, generate, upon detection of prepare signal 130, an initialize signal 140, and transmit initialize signal 140 to receiver panel 115. Processor 805 may further condition initialize signal 140, and, as a result of the conditioning, (a) transmit initialize signal 140 to receiver panel 115 at a particular time or after a predetermined period of time, and/or (b) maintain transmission of initialize signal 140 to receiver panel 115 for a predetermined period of time.

The term "module" is used herein to denote a functional operation that may be embodied either as a stand-alone component or as an integrated configuration of a plurality of sub-ordinate components. Thus, program module 815 may be implemented as a single module or as a plurality of modules that operate in cooperation with one another. Moreover, although program module 815 is described herein as being installed in memory 810, and therefore being implemented in software, it could be implemented in any of hardware (e.g., electronic circuitry), firmware, software, or a combination thereof.

Although retrofit device 120F is described herein as having the instructions for the method of the present invention installed into memory 810, the instructions can be embodied on an external tangible computer-readable storage medium, e.g. storage device 820, for subsequent loading into memory 810. Storage device 820 can be any conventional storage device, including, but not limited to, a floppy disk, a compact disk, a magnetic tape, a read only memory, an optical storage medium, universal serial bus (USB) flash drive, a digital versatile disc, or a zip drive. Storage device 820 could also be embodied as a random access memory, or other type of electronic storage device, located on a remote storage system (not shown) and coupled to memory 810 via a data communication network (not shown).

As mentioned above, retrofit device 120F is a computer device. As such, it processes data that is represented in digital form, at digital voltage levels. In practice, if prepare signal 130 is not a digital signal, and/or if initialize signal 140 is not a digital signal, retrofit device would then include circuitry to convert prepare signal 130 to a digital voltage level, and/or circuitry to provide initialize signal 140 at an appropriate voltage level.

Figure 9A:
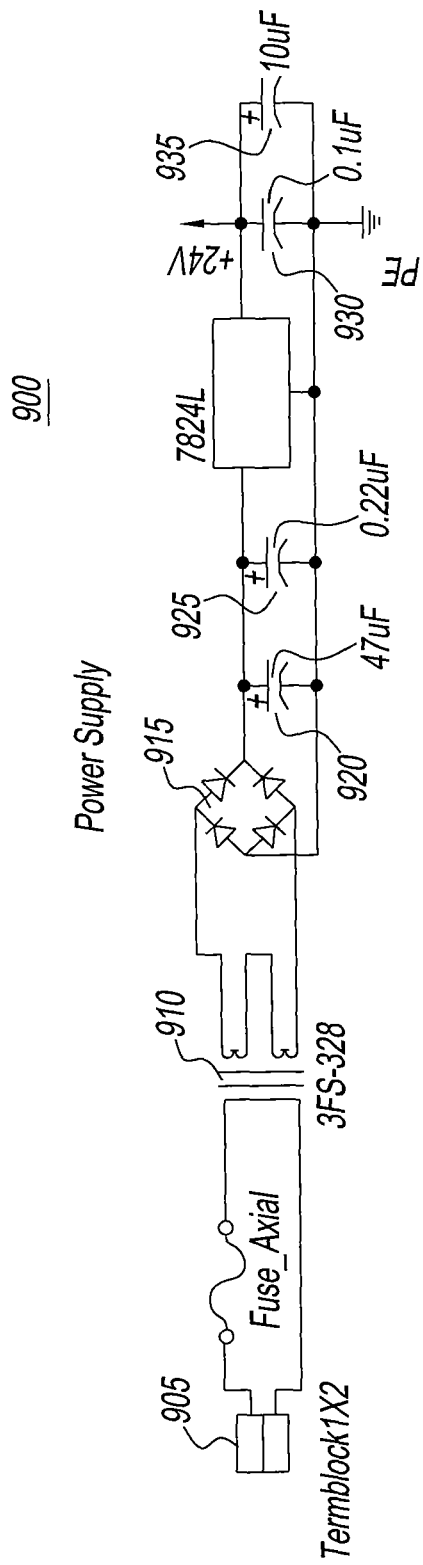
FIG. 9A is a schematic diagram of a power supply that complies with a voltage and a current requirement of a receiver panel.

FIG. 9A is a schematic diagram of a power supply 900 that complies with a voltage and a current requirement of receiver panel 115. Power supply 900 provides power that enables receiver panel 115 to operate. Typically, power supply 900 is a 12 to 24 direct current (DC) voltage source capable of providing 10 milliamperes (mA) of current. Power supply 900 includes a mains power input 905, a step down transformer 910 rated for 28 VAC, a full wave bridge rectifier 915, and filter capacitors 920, 925, 930 and 935 to output a DC signal, e.g., +24V. This DC signal resets receiver panel 115.

Figure 9B:
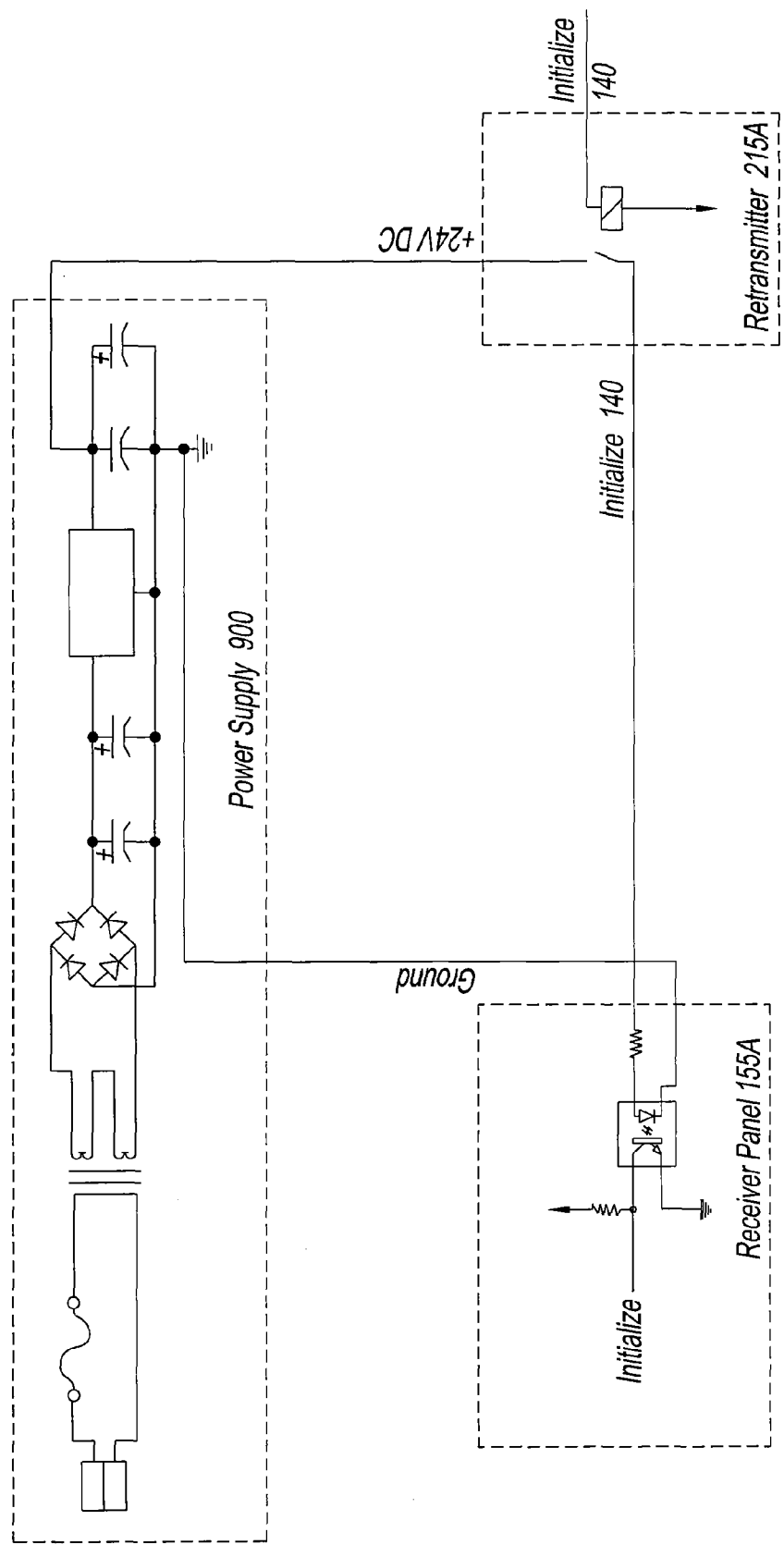
FIG. 9B is a schematic diagram of a power supply that is part of a receiver panel.

FIG. 9B is a schematic diagram of a circuit in which a power supply 900 operates in cooperation with receiver panel 115A and re-transmitter 215A. Power supply 900 may be included as part of receiver panel 115, where power supply 900 receives initialize signal 140 and resets receiver panel 115. In an alternative embodiment, power supply 900 may be integrated as part of retrofit device 120, where the DC signal is transmitted from power supply 900 to receiver panel 115 and serves as initialize signal 140.

Although power supply 900 is illustrated herein as producing +24 VDC, in practice, it can be configured to produce any suitable voltage or voltages required for operation with various embodiments of retrofit device 120 and receiver panel 115.

Figure 10:
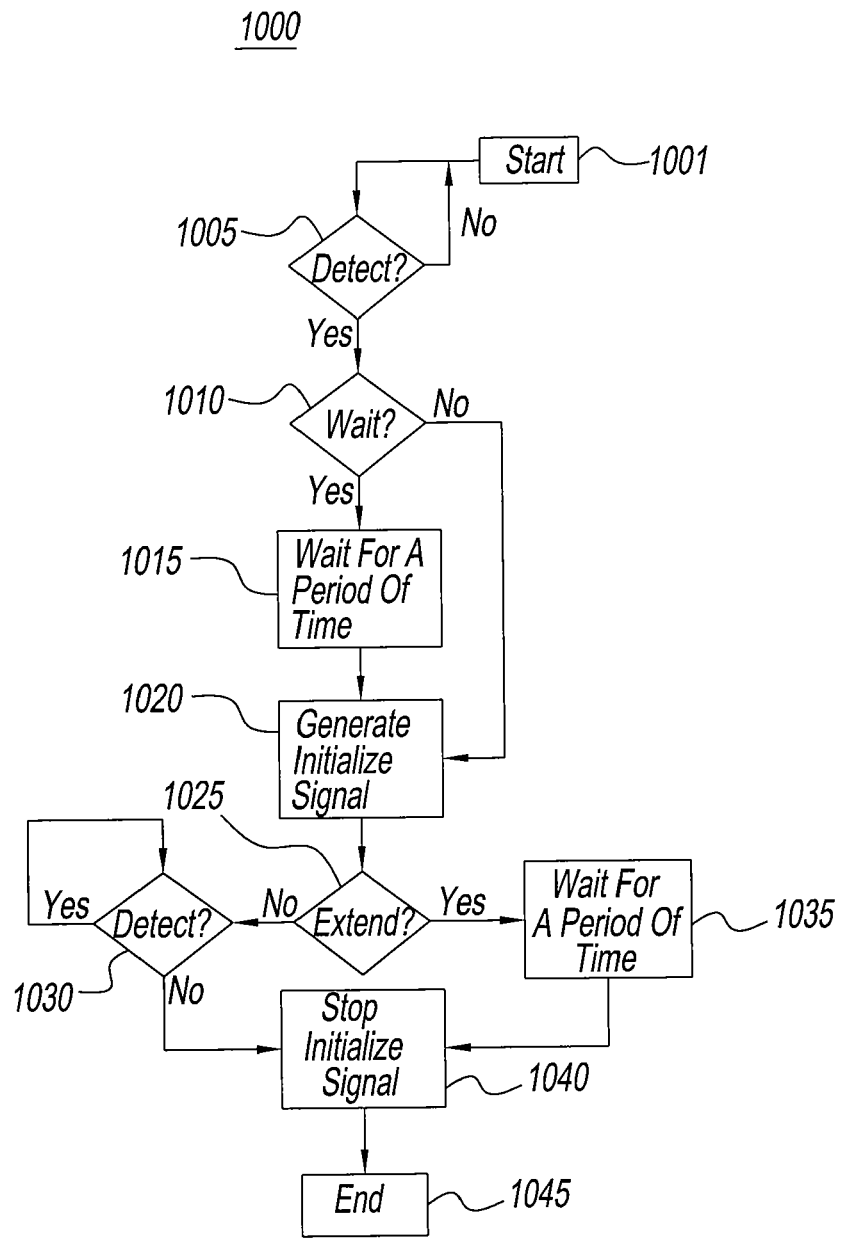
FIG. 10 is a flowchart of a method for x-ray radiography using a digital retrofit device.

FIG. 10 is a flowchart of a method 1000 for x-ray radiography using a digital retrofit device. Method 1000 is performed by retrofit device 120 and starts at step 1001, from which it progresses to step 1005.

In step 1005, retrofit device 120 awaits prepare signal 130. If retrofit device 120 does not detect prepare signal 130, method 1000 waits in step 1005. When retrofit device 120 detects prepare signal 130, method 1000 progresses to step 1010.

In step 1010, retrofit device 120 considers whether there should be a wait period prior to transmission of initialize signal 140, to allow time for x-ray generator 110 to build a charge, as discussed, for example, with reference to FIG. 7B. If there should be a wait period, method 1000 progresses to step 1015. If there should not be a wait period, method 1000 progresses to step 1020.

In step 1015, retrofit device 120 allows for a wait period of a predetermined period of time, e.g., 1750 ms, to elapse. The wait period can be controlled, for example, by utilization of an analog timing circuit, for example as employed by signal conditioner 210B, or by utilization of a digital timer implemented by processor 805. After the passage of the wait period in step 1015, method 1000 progresses to step 1020.

In step 1020, retrofit device 120 generates initialize signal 140. After step 1020, method 1000 progresses to step 1025.

In step 1025, retrofit device 120 considers whether to extend transmission of initialize signal 140, as discussed, for example, with reference to FIG. 7A. If initialize signal 140 should not be extended, method 1000 progresses to step 1030. If initialize signal 140 should be extended, method 1000 progresses to step 1035.

In step 1030, retrofit device 120 awaits disappearance of prepare signal 130. If retrofit device detects prepare signal 130, method 1000 waits in step 1030. When retrofit device 120 no longer detects prepare signal 130, method 1000 progresses to step 1040.

In step 1035, retrofit device 120 maintains initialize signal 140 for a predetermined period of time, e.g., 3250 ms, which is preferably greater than or equal to the period of time for the x-ray exposure. After step 1035, method 1000 progresses to step 1040.

In step 1040, retrofit device 120 stops producing initialize signal 140. Thereafter, method 1000 progresses to step 1045.

In step 1045, method 1000 ends.

Figure 11:
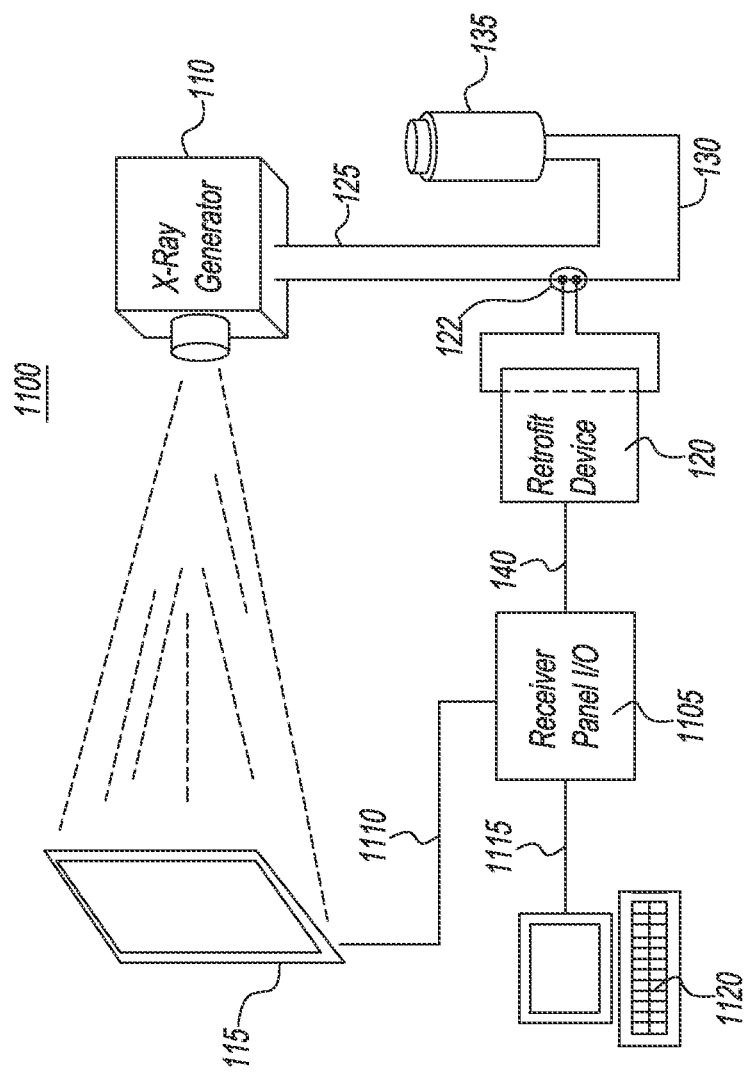
FIG. 11 is a block diagram of another embodiment of a digital retrofit x-ray system.

FIG. 11 is a block diagram of another embodiment of a digital retrofit x-ray system, designated as system 1100.

System 1100, is similar to system 100, but further includes a receiver panel input/output (I/O) 1105 and a computer 1120. As mentioned above with reference to FIG. 9, receiver panel 115 may require a dedicated power supply 900. Receiver panel I/O 1105 incorporates power supply 900 and provides power to receiver panel 115 by way of a receiver I/O signal 1110.

Receiver I/O signal 1110 transmits and receives signals, e.g., reset signals and data, to/from receiver panel I/O 1105 and receiver panel 115. In operation, receiver panel I/O 1105 receives initialize signal 140 from retrofit device 120 and transmits receiver I/O signal 1110 to receiver panel 115. Receiver I/O signal 1110, when received at receiver panel 115, triggers an initialization or reset.

Receiver panel 115 also transmits data via receiver I/O signal 1110 to receiver panel I/O 1105. For example, after an exposure, receiver panel 115 transmits exposure data, e.g., image data, via receiver I/O signal 1110 to receiver panel I/O 1105. Receiver panel I/O 1105 transmits the exposure data, by way of a data signal 1115, to computer 1120. Computer 1120 processes data signal 1115 and displays information provided by receiver panel 115, e.g., an x-ray image of the exposure.

In alternative embodiments, receiver panel I/O 1105 may be incorporated into retrofit device 120 such that retrofit device 120 produces a single initialize signal 140 that is compatible with receiver panel 115. Further, receiver panel I/O 1105 may be incorporated into receiver panel 115. In these embodiments, receiver panel 115 will receive initialize signal 140 and, internally, produce receiver I/O signal 1110, resulting in a reset of receiver panel 115.

FIG. 12 is a timing diagram for several signals of system 100. The diagram embodies an example of one complete preparation and exposure cycle of system 100. After one cycle is completed, receiver panel 115 produces one digital image. A further cycle may be initiated at any time after a previous cycle has finished. The operator initiates a cycle by actuating prepare switch 325 to produce prepare signal 130, which is detected by retrofit device 120. The operation of x-ray generator 110, including the generator charging and x-ray functions, occur independently from the reset function of receiver panel 115 delivered by retrofit device 120. Any x-ray emissions that illuminate receiver panel 115 during the time window labeled "Receiver X-Ray Window" are contributed to the image produced by receiver panel 115 at the end of the cycle.

The techniques described herein are exemplary, and should not be construed as implying any particular limitation on the present disclosure. It should be understood that various alternatives, combinations and modifications could be devised by those skilled in the art. For example, steps associated with the processes described herein can be performed in any order, unless otherwise specified or dictated by the steps themselves. The present disclosure is intended to embrace all such alternatives, modifications and variances that fall within the scope of the appended claims. In addition, the terms "comprises" or "comprising" are to be interpreted as specifying the presence of the stated features, integers, steps or components, but not precluding the presence of one or more other features, integers, steps or components or groups thereof.

What is claimed is:

1. A method comprising:
   detecting, during an exposure cycle of an x-ray system, prior to a generation of an x-ray by an x-ray generator during said exposure cycle, at a point on a cable that runs from a controller to said x-ray generator, a prepare signal that is being transmitted from said controller on said cable and being received by said x-ray generator on said cable to prepare said x-ray generator to generate said x-ray; and
   transmitting, in response to said detecting, an initialize signal that causes a reset of a digital receiver panel that prepares said digital receiver panel to capture said x-ray.

2. The method of claim 1, wherein said x-ray generator generates said x-ray after an energization period during which said x-ray generator builds a charge to produce said x-ray.

3. The method of claim 1, further comprising:
   waiting, after said detecting, for a predetermined period of time to elapse before commencing said transmitting.

4. The method of claim 1, wherein said transmitting comprises:
   maintaining transmission of said initialize signal for a predetermined period of time.

5. The method of claim 4, wherein said period of time is equal to or greater than a period of time for an x-ray exposure.

6. An apparatus comprising:
   a detector that detects, during an exposure cycle of an x-ray system, prior to a generation of an x-ray by an x-ray generator during said exposure cycle, at a point on a cable that runs from a controller to said x-ray generator, a prepare signal that is being transmitted from said controller on said cable and being received by said x-ray generator on said cable to prepare said x-ray generator to generate said x-ray, thus yielding a detected signal; and
   a transmitter that transmits, in response to receipt of said detected signal, an initialize signal that causes a reset of a digital receiver panel that prepares said digital receiver panel to capture said x-ray.

7. The apparatus of claim 6, wherein said x-ray generator generates said x-ray after an energization period during which said x-ray generator builds a charge to produce said x-ray.

8. The apparatus of claim 6, further comprising:
   a circuit that causes a delay of a predetermined period of time, between detection of said prepare signal and transmission of said initialize signal.

9. The apparatus of claim 6, wherein said transmitter maintains transmission of said initialize signal for a predetermined period of time.

10. The apparatus of claim 9, wherein said period of time is equal to or greater than a period of time for an x-ray exposure.

11. A non-transitory storage device comprising instructions that are readable by a processor and cause said processor to:
    detect, during an exposure cycle of an x-ray system, prior to a generation of an x-ray by an x-ray generator during said exposure cycle, at a point on a cable that runs from a controller to said x-ray generator, a prepare signal that is being transmitted from said controller on said cable and being received by said x-ray generator on said cable to prepare said x-ray generator to generate said x-ray; and
    transmit, in response to detecting said prepare signal, an initialize signal that causes a reset of a digital receiver panel that prepares said digital receiver panel to capture said x-ray.

12. The non-transitory storage device of claim 11, wherein said x-ray generator generates said x-ray after an energization period during which said x-ray generator builds a charge to produce said x-ray.

13. The non-transitory storage device of claim 11, wherein said instructions also cause said processor to:
    wait, after detection of said prepare signal, for a predetermined period of time to elapse before commencing said transmitting.

14. The non-transitory storage device of claim 11, wherein said instructions also cause said processor to:
    maintain transmission of said initialize signal for a predetermined period of time.

15. The non-transitory storage device of claim 14, wherein said period of time is equal to or greater than a period of time for an x-ray exposure.

16. A system comprising:
    an x-ray generator that, in response to a receipt of a prepare signal, builds a charge to produce an x-ray, and in response to a receipt of an expose signal, produces said x-ray;
    a digital receiver panel that, in response to a receipt of an initialize signal, performs a reset operation that prepares said digital receiver panel to capture said x-ray;
    a controller that generates said prepare signal;
    a cable that runs from said controller to said x-ray generator and couples said prepare signal from said controller to said x-ray generator; and
    an apparatus that detects said prepare signal at a point on said cable during an exposure cycle, while said prepare signal is being transmitted from said controller on said cable and being received by said x-ray generator on said cable, prior to a generation of said x-ray by said x-ray generator during said exposure cycle, and upon detection of said prepare signal, generates said initialize signal.

\* \* \* \* \*